United States Patent [19]

Burgin

[11] 4,344,419

[45] Aug. 17, 1982

[54] ACRYLOOPTIC TONGUE DEPRESSOR AND HANDLE THEREFOR

[76] Inventor: Kermit Burgin, R.R. #1, Box 334, Whitestown, Ind. 46075

[21] Appl. No.: 105,509

[22] Filed: Dec. 20, 1979

[51] Int. Cl.³ .................................................. A61B 1/06
[52] U.S. Cl. ............................................. 128/18; 128/3
[58] Field of Search ....................................... 128/3–22

[56] References Cited

U.S. PATENT DOCUMENTS

| 2,690,745 | 10/1954 | Govan | 128/15 |
| 3,890,960 | 6/1975 | Wansch et al. | 128/16 |
| 3,916,881 | 11/1975 | Heine | 128/16 |

FOREIGN PATENT DOCUMENTS 2302614  1/1973  Fed. Rep. of Germany.

*Primary Examiner*—Henry J. Recla
*Assistant Examiner*—T. J. Wallen

*Attorney, Agent, or Firm*—Jenkins, Coffey, Hyland, Badger & Conard

[57] ABSTRACT

A combination handle unit and tongue depressor includes a light source and a means for attaching a light-transmissive disposable depressor member to the handle to conduct light from the source into, for example, the mouth and throat of a patient being examined. In some illustrated embodiments, the attachment means includes a peripheral groove about a portion of the handle unit into which the depressor member may be inserted. In some embodiments, the attachment means includes pins or posts provided on one of the handle unit or tongue depressor, and cooperating sockets for receiving the posts formed on the other of the handle unit or tongue depressor. The handle unit is conveniently designed and configured to remain out of the line of sight of the examining physician into the mouth, throat, or the like, of the patient being examined. To permit removal of the depressor member from the handle without the physician having to touch it, the handle is provided with a trigger for ejecting the depressor member.

7 Claims, 7 Drawing Figures

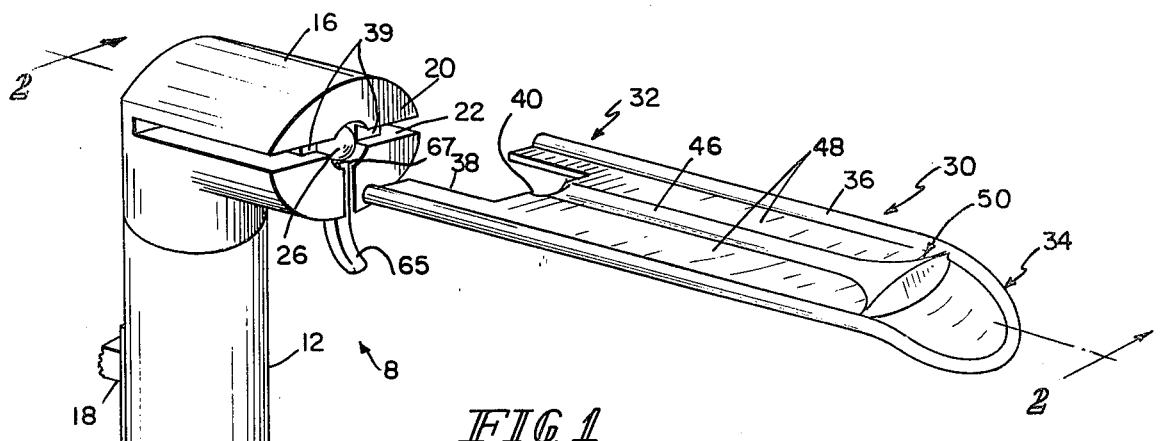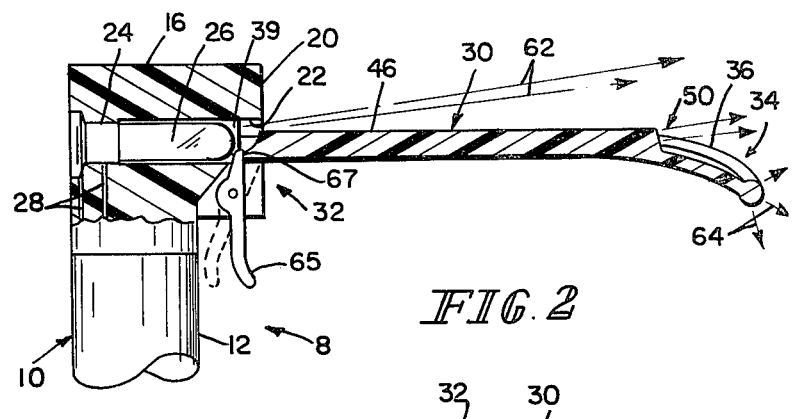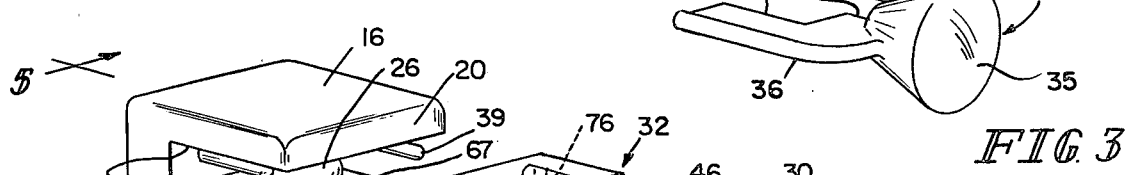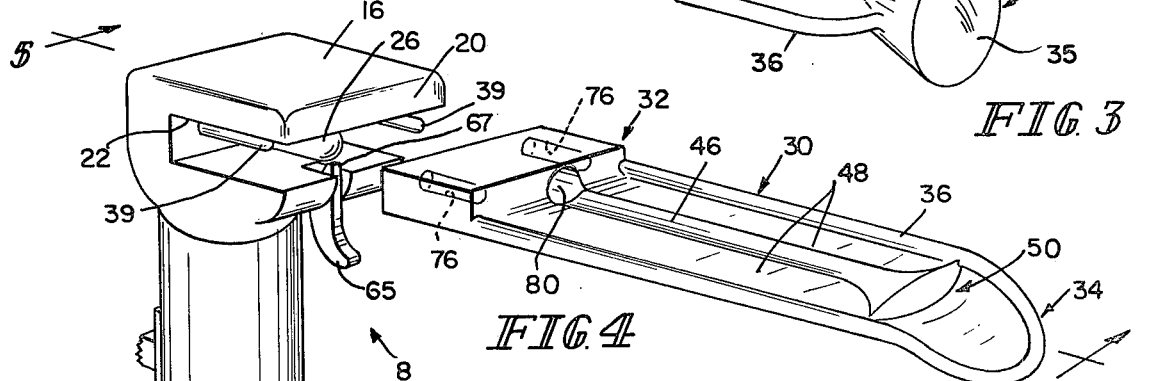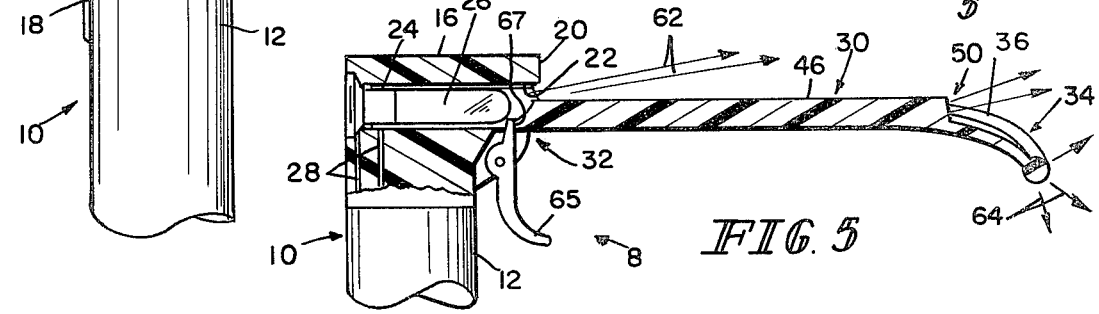

ACRYLOOPTIC TONGUE DEPRESSOR AND HANDLE THEREFOR

This is a related application to my application Ser. No. 958,795, filed Nov. 8, 1978, which is a continuation-in-part of my application Ser. No. 811,550, now U.S. Pat. No. 4,165,746; my application Ser. No. 958,794, filed Nov. 8, 1978, now U.S. Pat. No. 4,263,899 which is a continuation-in-part of my application Ser. No. 901,521, now U.S. Pat. No. 4,156,424; and my application Ser. No. 10,751, filed Feb. 9, 1979.

This invention relates to medical examination instruments, and specifically to tongue depressors.

In the past, when examining the mouth, throat, and surrounding tissues, it has been customary to depress the tongue with a depressor held in one hand and to illuminate the mouth and throat of a patient with a light source held in the other hand. Aside from the awkwardness of requiring both hands, the apparatus of the prior art requires that the light source be held close to the examiner's line of sight, or even that the user look through a hole provided in an examining instrument containing the light source.

Various types of medical examination instruments utilizing fiber optic or acrylooptic light transmission to illuminate a body orifice, meatus, or incision for examination or the like, are known. There are, for example the disclosures of the following U.S. Pat. Nos.: 3,664,330; 3,762,400; 3,796,214; 3,716,047; 3,890,961; 2,247,258; 4,086,919; 3,851,642; 3,592,199; 3,324,850; 3,131,690; 2,482,971 and 3,978,850.

Attention is specifically directed to German Offenlegungsschrift No. 2,302,614 and U.S. Pat. No. 2,690,745.

Briefly, the invention comprises an examination instrument having a handle, a light source, a light-transmissive examination member, and means for attaching the light-transmissive examination member to the handle. The attachment means includes a means for directing a portion of the light through the examination member to have the examination member transmit light to the region being examined to illuminate such region. The illustrative examination instrument comprises a tongue depressor, constructed from some light-transmissive material such as LUCITE® or PLEXIGLAS®, for use with a combination handle and light source unit. Such a depressor is constructed so that light from the source is directed through the light-transmissive material of the depressor and is adapted at a proximal end to be attached to such handle unit.

The invention may be best understood by reference to the following description and accompanying drawings which illustrate the invention. In the drawings:

FIG. 1 is a perspective view of an apparatus constructed according to the invention;

FIG. 2 is a sectional view of the apparatus of FIG. 1, taken generally along section lines 2—2 thereof;

FIG. 3 is a perspective view of another light-transmissive member constructed according to the invention;

FIG. 4 is a perspective view of another apparatus constructed according to the present invention;

FIG. 5 is a sectional view of the apparatus of FIG. 4, taken generally along section lines 5—5 thereof;

Figure 6:
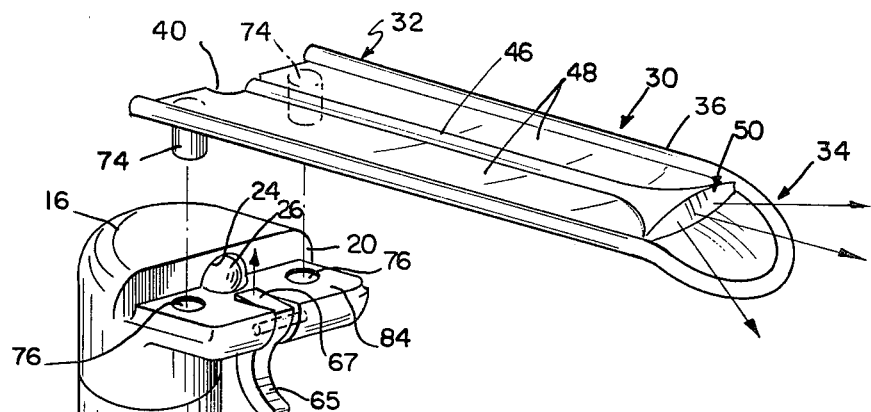
FIG. 6 is a perspective view of another embodiment of the present invention.

Referring to FIG. 1, a medical examination instrument 8 includes a base 10 having a tubular handle 12, a threaded bottom cap 14, and a head 16. Handle 12 serves to hold one or more electric cells (not shown) which provide a power source. A multi-position switch 18 controls delivery of power from the cells. Head 16 is provided with a forwardly extending face 20 and a groove 22 which extends perimetrally about the sides and face 20 of head 16.

Referring now to FIG. 2, head 16 provides a socket 24 which receives an electric light bulb 26. Conductors 28, which illustratively are molded into the plastic material from which head 16 is formed, supply power through switch 18 from the cells to bulb 26.

As may be seen in both FIG. 1 and FIG. 2, a member 30, shown in a form suited for use as a tongue depressor, has a proximal end 32 and a downwardly turned and slightly concave distal end 34. Different concavities, curvatures, etc., can be provided so that an examining physician can select a member 30 to meet the requirements of a specific examination. A beaded edge 36 is provided about the perimeter of member 30 except along the edge of proximal end 32. A notch 38 is provided in the edge of proximal end 32 to clear the bulb enclosure portion 39 of head 16 so that member 30 can be inserted into groove 22 of head 16 where it will be frictionally retained. A cut-out 40 provides clearance for bulb 26.

Head 16 can be constructed from an opaque plastic material and can be provided with highly reflective surfaces, especially those surfaces in contact with member 30 and the surface of face 20. Such surfaces can be, for example, metal plated to provide mirror-like reflective surfaces. Member 30 should be made of a light-transmissive material such as polymethylmethacrylate (e.g., LUCITE® or PLEXIGLAS®), and is preferably quite inexpensively constructed so as to be disposable. To this end, member 30 is provided with a central reinforcing and light-concentrating rib 46. Rib 46 cooperates with the bead 36 to provide longitudinal stiffness to member 30. This permits the web regions 48 between the bead 36 and rib 46 to be made quite thin, conserving on the amount of light-transmissive material required to construct the members 30 to achieve a desired strength, and therefore reducing the cost of such members 30.

In accordance with the teachings of my above identified U.S. patent application Ser. No. 10,751, a lens 50 for directing the light transmitted down rib 46 is provided adjacent distal end 4 of member 30. To meet the specific requirements of a particular application, lens 50 can be made to focus or to diffuse the light to provide the necessary illumination in the mouth, throat, etc.

To use the apparatus of FIGS. 1-2, the user attaches a member 30 having the desired configuration, lens characteristics, etc., to head 16 by sliding the proximal end of the seleted member 30 into groove 22 of head 16. The portion of beaded edge 36 adjacent proximal end 32 aids in guiding member 30 into groove 22 and in retaining it there after insertion. The user then adjusts switch 18 to provide a desired amount of light. Holding the apparatus by handle 12, member 30 is inserted into the patient's mouth and pressed downward against the upper surface of the patient's tongue in a manner similar to a conventional tongue depressor.

As illustrated in FIG. 2, some of the light from bulb 26 passes above the surface of member 30, along rays 62, and illuminates the mouth and throat. Some of the light passes through the light-transmissive material of member 30 and is emitted from the lens 50 as well as along rays 64 at the distal end 34 of member 30, to illuminate the remote lower portions of the throat and the openings of the esophagus and trachea. Some of the light passing through the planar portion of member 30 does not pass from the member 30 along a linear path. Rather than passing out of member 30 where the downward curve of distal portion 34 begins, some of the light is "bent" to follow the curvature of member 30 and be conducted to the extreme end of distal portion 34. This phenomenon, combined with the disclosed apparatus, permits the user to view areas of the mouth and throat which might otherwise be difficult to view using the apparatus of the prior art. It is convenient and desirable for a physician, after conducting a throat examination or the like, not to have to handle the depressor member 30 in order to remove it from the handle 12. In furtherance of this objective, a trigger 65 is pivotally mounted in head 16 and includes a camming surface 67 which rides against member 30. When the trigger is depressed, e.g., by the examining physician's forefinger, the camming surface 67 is urged against the rearward end 32 edge of member 30 to eject it from groove 22. The trigger 65 must be sufficiently sturdily built to overcome the frictional engagement of member 30 in head 16.

In the discussion of the other various embodiments illustrated, those elements numbered identically with the elements of FIGS. 1-2 perform the same or similar functions.

FIG. 3 illustrates another embodiment of the member 30. Here, member 30 has a proximal end 32 having a window 38 and a notch 40. A beaded edge 36 is provided along the two opposite sides of member 30. Distal end 34 is provided with a concave surface (not shown) which is positioned adjacent to lamp 26 (FIGS. 1-2), and expands in a somewhat frustoconical shape to a convex surface 35 of a lens 50. The embodiment of FIG. 3 is believed useful, for example, for examining nasal passages or the ear canal.

FIGS. 4 and 5 illustrate another means of attaching the tongue depressor member 30 to the head 16. In this embodiment, head 16 is attached to handle 12 and a deep channel 22 is cut across the entire front surface 20 of head 16. Two sturdy posts 74 are located in channel 22 on opposite sides of bulb 26. Member 30 is similar to the member 30 of FIGS. 1-2, except that the proximal end 32 of member 30 in FIGS. 4-5 is constructed generally as a right rectangular prism having two sockets 76 for receiving posts 74 and a large socket 80 for lamp 26. When member 30 is pressed onto head 16, posts 74 fit into sockets 76, guiding member 30 into place and frictionally retaining it. Bulb 26 fits loosely into socket 80. As with the embodiment of FIGS. 1-2, a portion of the light passes over member 30 and the remainder passes through member 30 to be directed from lens 50 as well as distal end 34.

FIG. 6 illustrates yet another means of attaching a member 30 to a head 16. In this embodiment, head 16 is attached to handle 12 and a lip 84 projects forward from head 16 across the entire front surface 20 of head 16. Two sturdy posts 74 project downwardly from the underside of member 30 adjacent end 32. Lip 84 is provided with a pair of large upwardly opening sockets 76 for receiving posts 74. When member 30 is pressed onto head 16, posts 74 fit into sockets 76, guiding member 30 into place and frictionally retaining it. As with the embodiments of FIGS. 1-2 and 4-5, a portion of the light passes over member 30 and the remainder passes through member 30, to be transmitted from lens 50 and at distal end 34. In this embodiment, the ejecting trigger 65 camming surface 67 is provided on top of trigger 65 to urge upwardly on the underside of contacting member 30 to disengage posts 74 from sockets 76.

Figure 7:
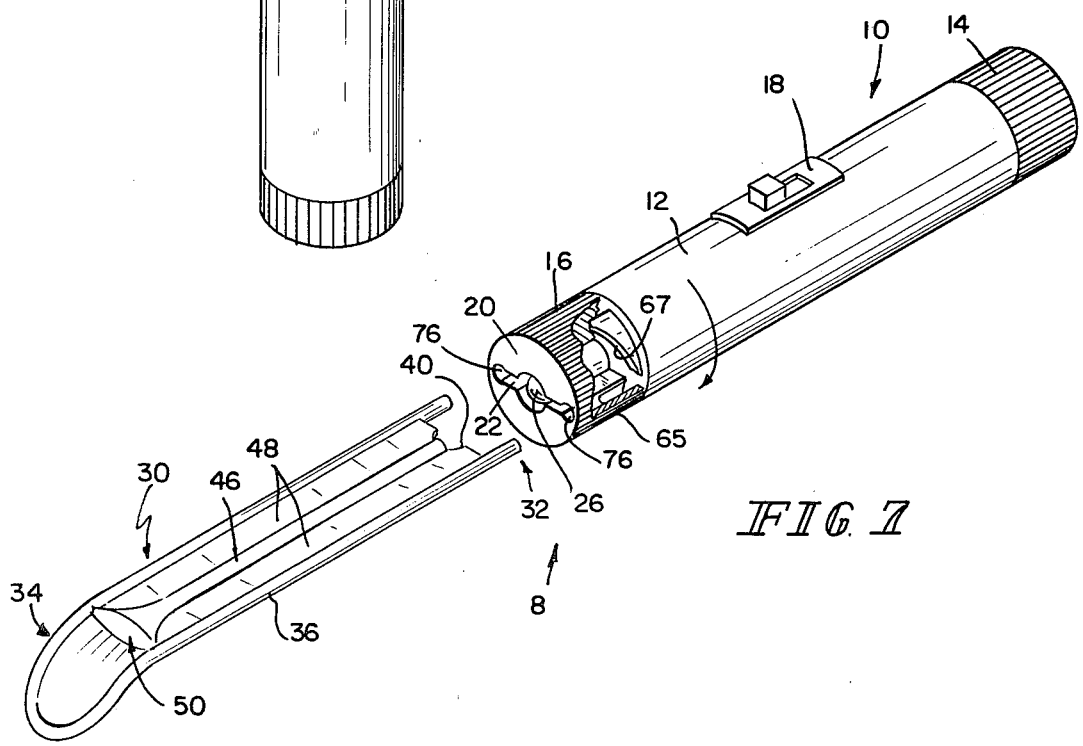
FIG. 7 is a perspective view of yet another embodiment of the present invention.

In all of the above-discussed embodiments, a generally right-angle orientation between the handle 12 and the tongue depressor member 30, as well as the design of head 16, insures that the apparatus 8 will be generally out of the line of sight of the Examiner into the mouth and throat of the patient being examined. In certain circumstances, however, it may not be necessary, desirable, convenient, or possible to use an apparatus 8 having such an angular orientation between the handle 12 and member 30. To these situations, the instrument 8 of FIG. 7 is addressed. In this embodiment, the head 16 and handle 12 are formed in a generally right circular cylindrical "flashlight" configuration. A deep channel 22 is provided in the front surface 20 of head 16. Two sockets 76 are provided at the transverse ends of channel 22 on opposite sides of a somewhat larger socket housing bulb 26. Two sturdy posts 74 project rearwardly from member 30 adjacent end 32. Posts 74 in this embodiment are adequately reinforced extensions of the bead 36. When member 30 is pressed onto head 16, posts 74 fit into sockets 76, guiding member 30 into place and frictionally retaining it. As with the embodiment of FIGS. 1-2, 4-5, and 6, a portion of the light passes over member 30 and the remainder passes through member 30, to be transmitted from lens 50 and at distal end 34. The ejection trigger 65 of this embodiment is incorporated into head 16. The head 16, including groove 22 and sockets 76, is mounted on handle 12 for pivotal movement about the axis of symmetry of handle 12. Bulb 26 is stationarily positioned on the handle 12 axis. The forward wall 110 of handle 12, which is covered by head 16, is provided with a pair of forwardly projecting ears 112, only one of which is illustrated in FIG. 7. The forwardmost surface of each ear 112 provides the camming surface 67. As head/trigger 16/65 is rotated during ejection, the remote ends of posts 74 are cammed forwardly by surfaces 67 until posts 74 are disengaged from sockets 76 to eject member 30 from head 16.

What is claimed is:
1. An examination instrument, comprising
a base unit having a handle portion and a head portion, said head portion comprising a first front surface and two side surfaces adjacent the front surface;
a light source mounted in the head portion for providing light in the head portion of said base unit;
a light-transmissive examination member for contacting a body surface to be examined;
a means for removably attaching and securing the examination member to the head portion of the base unit such that said examination member is attached adjacent the light source, said attachment means including means providing a peripheral groove extending completely across said first front surface, and at least partially across said two side surfaces, said examination member including a proximal end portion complementally configured to said peripheral groove for insertion into the groove.

2. An examination instrument, comprising
a base unit having a handle portion and a head portion, said head portion comprising a first front surface and two side surfaces adjacent the front surface;
a light source mounted in the head portion for providing light in the head portion of said base unit;
a light-transmissive examination member for contacting a body surface to be examined;
a means for removably attaching the examination member to the head portion of the base unit such that said examination member is attached adjacent the light source, said examination member including a proximal end portion having an opening therein,
said attachment means including a post member provided on the head portion of said base unit and extending therefrom, said post being sized and positioned to be received by said opening on the examination member for guiding, positioning, and maintaining the examination member upon the head portion of the base unit;
a means for selectively disengaging said examination member from the head portion of said base unit, said selective disengagement means including a trigger movably mounted on the head, a cam means actuable by the trigger to disengage said member from said head,
said trigger and cam means being positioned on the base unit so that actuation of the trigger causes the cam means to apply pressure to the examination member in substantially the same direction as the post extends.

3. An examination instrument, comprising
a base unit having a handle portion and a head portion, said head portion comprising a first front surface and two side surfaces adjacent the front surface;
a light source mounted in the head portion for providing light in the head portion of said base unit;
a light-transmissive examination member for contacting a body surface to be examined;
a means for removably attaching the examination member to the head portion of the base unit such that said examination member is attached adjacent to the light source, said head portion having an opening therein,
said attachment means having a post member provided on the proximal end of the examination member and extending therefrom, said post being sized and positioned to be received in said opening, the reception of said post into said opening serving to guide, position, and maintain the examination member upon the head portion of the base unit;
a means for selectively disengaging said examination member from the head portion of said base unit, said selective disengagement means including a trigger movably mounted on the head, a cam means actuable by the trigger to disengage said member from said head,
said trigger and cam means being positioned on the base unit so that actuation of the trigger causes the cam means to apply pressure to the examination member in substantially the same direction as the post extends.

4. An examination instrument, comprising
a base unit having a handle portion and a head portion, said head portion comprising a first front surface and two side surfaces adjacent the front surface;
a light source mounted in the head portion for providing light in the head portion of said base unit;
a light-transmissive examination member for contacting a body surface to be examined;
a means for removably attaching the examination member to the head portion of the base unit such that said examination member is attached adjacent the light source, said attachment means including means providing a peripheral groove extending completely across said first front surface, and at least partially across said two side surfaces, said examination member including a proximal end portion complementary interfitting the groove,
a means for selectively disengaging said examination member from the head portion of said base unit, said selective disengagement means including a trigger movably mounted on the head, a cam means coupled to said trigger and selectively actuable by manipulation of the trigger to disengage said examination member from said head.

5. An examination instrument, comprising
a base unit having a handle portion providing a hand grip and a head portion;
a light source mounted in the head portion for providing light in the head portion of said base unit;
a light-transmissive examination member having a proximal end for engaging the head portion of the base unit and a distal end for contacting a body surface to be examined;
a lens formed on the examination member for directing light onto the body surface being examined;
a means for removably attaching the proximal end of the examination member to the head portion of the base unit such that said examination member is attached adjacent the light source;
attachment means including a post member provided on the head portion and extending therefrom, said post being sized and positioned to be received by a complementary interfitting opening on the examination member for guiding, positioning, and maintaining the examination member upon the head portion of the base unit;
means for selectively disengaging said examination member from the head portion of said base unit, said selective disengagement means including a trigger movably mounted on the head, a cam means coupled to the trigger, said cam means being actuable by the trigger to disengage said member from said head,
said trigger and cam means being positioned on the base unit so that actuation of the trigger causes the cam to apply pressure to the examination member in substantially the same direction as the post extends.

6. An examination instrument, comprising
a base unit having a handle portion providing a hand grip and a head portion;
a light source mounted in the head portion for providing light in the head portion of said base unit;
a light-transmissive examination member having a proximal end for engaging the head portion of the base unit and a distal end for contacting a body surface to be examined;
a lens formed on the examination member for directing light onto the body surface being examined;

a means for removably attaching the proximal end of the examination member to the head portion of the base unit such that said examination member is attached adjacent the light source, said attachment means including a post member sized and positioned to be received by a complementary interfitting opening, the reception of said post into said opening serving to guide, position and maintain the examination member upon the head portion of the base unit;

means for selectively disengaging said examination member from the head portion of said base unit, the selective disengagement means including a trigger movably mounted on the head, a cam means coupled to the trigger, said cam means being actuable by the trigger to disengage said member from said head, said trigger and cam means being positioned on the base unit so that actuation of the trigger causes the cam to apply pressure to the examination member in substantially the same direction as the post extends.

7. An examination instrument, comprising a base unit having a handle portion providing a hand grip and a head portion;

a light source mounted in the head portion for providing light in the head portion of said base unit;

a light-transmissive examination member having a proximal end for engaging the head portion of the base unit and a distal end for contacting a body surface to be examined;

a lens formed on the examination member for directing light onto the body surface being examined;

a means for removably attaching the proximal end of the examination member to the head portion of the base unit such that said examination member is attached adjacent the light source;

a means for selectively disengaging said examination member from the head portion of said base unit, said selective disengagement means including a trigger movably mounted on the head, a cam means coupled to the trigger, said cam means being actuable by the trigger to disengage said examination member from said head.

* * * * *

UNITED STATES PATENT AND TRADEMARK OFFICE
CERTIFICATE OF CORRECTION

PATENT NO. : 4,344,419
DATED : August 17, 1982
INVENTOR(S) : Kermit H. Burgin

It is certified that error appears in the above-identified patent and that said Letters Patent is hereby corrected as shown below:

Column 2, line 51, "end 4" should be -- end 34 --; same column, line 58, correct the spelling of "selected".

Column 4, line 66 (Claim 1, line 18), change "complementally" to -- complementarily --.

Column 6, line 15 (Claim 4, line 18), change "complementary" to -- complementarily --; same column, line 42 (Claim 5, line 19), change "complementary" to -- complementarily --.

Column 7, line 6 (Claim 6, line 17), change "complementary" to -- complementarily --.

Signed and Sealed this

Sixteenth Day of November 1982

[SEAL]

Attest:

GERALD J. MOSSINGHOFF

Attesting Officer    Commissioner of Patents and Trademarks